United States Patent [19]
Castillo et al.

[11] Patent Number: 5,520,920
[45] Date of Patent: May 28, 1996

[54] USE OF CERTAIN ANIONIC SURFACTANTS TO ENHANCE ANTIMICROBIAL EFFECTIVENESS OF OPHTHALMIC COMPOSITIONS

[75] Inventors: Ernesto J. Castillo, Arlington; Yusuf Ali, Fort Worth, both of Tex.

[73] Assignee: Alcon Laboratories, Inc., Fort Worth, Tex.

[21] Appl. No.: 106,459

[22] Filed: Aug. 13, 1993

Related U.S. Application Data

[63] Continuation-in-part of Ser. No. 937,228, Aug. 28, 1992, abandoned.

[51] Int. Cl.$^6$ .......................... A01N 25/02; A01N 25/04; A01N 25/34; A61K 31/74
[52] U.S. Cl. ...................... 424/405; 424/78.04; 424/428; 514/912; 514/975
[58] Field of Search ................................ 424/427, 428, 424/78.04, 405; 514/912, 975

[56] References Cited

U.S. PATENT DOCUMENTS

| | | | |
|---|---|---|---|
| 3,275,503 | 9/1966 | Marnett et al. | 514/547 |
| 4,485,029 | 11/1984 | Kato et al. | 252/106 |
| 4,911,920 | 3/1990 | Jani et al. | 424/78.04 |
| 5,000,868 | 3/1991 | Wittpenn, Jr. et al. | 252/106 |

FOREIGN PATENT DOCUMENTS

| | | |
|---|---|---|
| 0194097 | 10/1986 | European Pat. Off. . |
| 0243145A2 | 10/1987 | European Pat. Off. . |
| 0429732 | 6/1991 | European Pat. Off. . |

*Primary Examiner*—Carlos Azpuru
*Attorney, Agent, or Firm*—Julie J. L. Cheng; Patrick M. Ryan

[57] ABSTRACT

Certain anionic surfactants are used to enhance antimicrobial effectiveness in comfortable, sustained release ophthalmic compositions containing polyelectrolytes, such as carboxyvinyl polymers, polystyrene sulfonic acid polymers and cationic exchange resins, as well as at least one active ingredient.

16 Claims, No Drawings

USE OF CERTAIN ANIONIC SURFACTANTS TO ENHANCE ANTIMICROBIAL EFFECTIVENESS OF OPHTHALMIC COMPOSITIONS

This a continuation-in-part of U.S. patent application Ser. No. 07/937,228 filed 28 Aug. 1992, now abandoned.

BACKGROUND OF THE INVENTION

The present invention relates generally to ophthalmic compositions. In particular, the present invention relates to the use of certain anionic surfactants, particularly modified sarcosinates and lactylates, to prevent or to reduce binding of the antimicrobial components of ophthalmic compositions to other components contained therein, thereby improving the antimicrobial efficacy of such compositions.

In recent years, a number of ophthalmic compositions have been introduced which contain a variety of components, such as carboxyvinyl polymers (e.g., Carbopol®), ion exchange resins (e.g., Amberlite®), or other large polyelectrolytes, which provide sustained release of the ophthalmic agent(s), as well as increased patient comfort. Such compositions are described, for example, in U.S. Pat. No. 4,911,920 (Jani et al.). Although these compositions are comfortable and have sustained release characteristics, cationic antimicrobials, such as benzalkonium chloride (BAC), which are often added as preservatives to such compositions tend to bind to the anionic molecules present in the formulations, resulting in loss of antimicrobial effectiveness.

Sarcosinate surfactants are composed of acylated sarcosines. Sarcosine ($CH_3$—NH—$CH_2$—COOH) is an amino acid derivative produced in the body for the synthesis of glycine ($NH_2$—$CH_2$—COOH), a basic amino acid. Common fatty acids and their derivatives utilized in the manufacture of sarcosinate surfactants are lauric, oleic, and myristic acids and their esters and halides. Because of their mildness, sarcosinate surfactants have been utilized in shampoos, mouthwashes, skin cleansers, sunscreens, aerosol shaving lathers and other personal care products. To date, the main applications of these types of surfactants have been in the cosmetic industry. For example, European Patent 194097 (Schmidt et al.), assigned to Procter & Gamble, mentions sodium lauroyl sarcosinate as the mild anionic surfactant utilized in an aerosol skin-cleansing and moisturizer mousse. Applicants are not aware of any ophthalmic use of these types of surfactants.

SUMMARY OF THE INVENTION

It has now surprisingly been found that the inclusion of certain anionic surfactants, particularly modified sarcosinates and lactylates, in the comfortable, sustained release compositions described above significantly reduces the above-cited binding problem. That is, addition of certain anionic surfactants to some commonly utilized ophthalmic compositions substantially enhances the antimicrobial efficacy of such compositions. Although the Applicants do not wish to be bound to a particular theory, it is believed that the addition of these anionic surfactants to the compositions result in the release of the bound preservative by the formation of a loose and reversible surfactant-preservative complex, which has antimicrobial effectiveness.

The compositions of the present invention have improved preservative efficacy but retain the desired characteristics of comfort and sustained release of the active ingredient(s). In preferred embodiments, the comfortable, sustained release compositions of the present invention comprise one or more modified sarcosinates or lactylates, an ophthalmic agent ("active"), a preservative and an ophthalmically acceptable carrier, which may include one or more polyelectrolytes.

DETAILED DESCRIPTION OF THE INVENTION

Preferred anionic surfactants of the present invention are certain modified sarcosinates having the following generic structure:

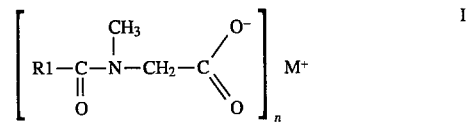

wherein: $R^1 = C_4$–$C_{27}$ saturated or unsaturated hydrocarbon;

M=H or a pharmaceutically acceptable salt; and n=1, 2 or 3.

In general, an amount of one or more sarcosinates of Structure I are used in the compositions of the present invention in an amount between about 0.005 and about 0.5 percent by weight (wt %), preferably between about 0.01 and about 0.2 wt %. It is most preferred to use between about 0.03 and about 0.12 wt % of one or more of these sarcosinates.

Also preferred are certain lactylates having the following generic structure:

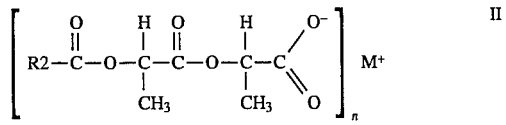

wherein: $R^2 = C_4$–$C_{27}$ saturated or unsaturated hydrocarbon;

M=H or a pharmaceutically acceptable salt; and n=1,2 or 3.

In general, one or more lactylates of Structure II may be used in the compositions in an amount between about 0.1 and about 5.0 wt %. It is preferred to use an amount between about 0.1 and about 2.0 wt %, and it is most preferred to use about 0.5 wt % of a lactylate of Structure II.

For purposes of this specification, the term "Surfactant" or "Surfactants" shall refer to the compounds of Structure I and/or II, except as otherwise indicated. The preferred Surfactants are sold under the Hamposyl® (W. R. Grace), Sarkosyl® and Medialan® (Ciba-Geigy) labels. Especially preferred are: lauroyl sarcosine (Hamposyl® L), oleoyl sarcosine (Hamposyl® O), myrstoyl sarcosine (Hamposyl® M), cocoyl sarcosine (Hamposyl® C), stearoyl sarcosine (Hamposyl® S), pelargodoyl sarcosine (Hamposyl® P) and sodium capryl lactylate (Pationic® 122A).

The Surfactants can be used in any ophthalmic compositions containing cationic antimicrobials which also contain polyelectrolytes such as high molecular weight, anionic mucomimetic polymers (e.g., carboxyvinyl polymers such as Carbopol®), polystyrene sulfonic acid polymers, cationic exchange resins (e.g., Amberlite® or Dowex®), or the like. Examples of suitable polyelectrolytes are detailed below.

The high molecular weight, anionic mucomimetic polymers useful in the present invention have a molecular weight between about 50,000 and 6 million. The polymers are characterized as having carboxylic acid functional groups and preferably contain between 2 and 7 carbon atoms per functional group. The gels which form during preparation of ophthalmic polymer dispersions have a viscosity between about 1,000 to about 300,000 centipoise (cps). Suitable polymers are carboxyvinyl polymers, preferably those called Carbomers, e.g., Carbopol® (B. F. Goodrich Co., Cleveland, Ohio). Specifically preferred are Carbopol® 934P, Carbopol® 974P and Carbopol® 940. Other suitable gelling polymers include: alginates, carrageenan, natural gumar (xanthan, karaya and tragacanth) and carboxy methyl cellulose. Such polymers will typically be employed in an amount between about 0.05 and about 8.0 wt %, depending on the desired viscosity of the composition. Pourable liquid compositions generally comprise an amount of the polymer between about 0.05 and about 2.0 wt %.

The cation exchange resins useful in the present invention are characterized as either strongly acidic, such as those having sulfonic acid or sulfuric acid functionality, or weakly acidic, such as those having carboxylic acid functionality. Such resins are readily available, for example, from Rohm & Haas (Philadelphia, Pa.) under the name Amberlite® and from Dow Chemical Co. (Midland, Mich.) under the name Dowex®. The average particle size of the commercially available forms of the resins is about 40 to 150 microns. As the particle size of the resin is critical, such commercially available particles are most conveniently reduced to a particle size range of about 1.0 to 25 microns by ball milling, according to known techniques. At least 95% of the resulting spheroidal particles must have a diameter less than 20 microns. The ion exchange resins will typically be present in an amount between about 0.05 to about 10.0 wt % and will have an average particle size diameter between about 1 to about 20 microns.

These anionic mucomimetic polymers and cation exchange resins are discussed in greater detail in U.S. Pat. No. 4,911,920 issued Mar. 27, 1990. The entire contents of that patent are hereby incorporated by reference herein.

The polystyrene sulfonic acid polymers (and their salts) useful in the compositions of the present invention have the following formula:

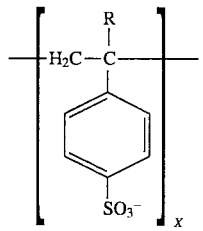

III wherein: R=H or CH$_3$; and

X=an integer such that the molecular weight of the polystyrene sulfonic acid polymer may vary from about 10,000 to 1.6 million.

In the preferred polystyrene sulfonic acids of Structure III, R=H and the molecular weight is between about 500,000 to about 1,000,000, preferably about 600,000. The polystyrene sulfonic acid polymers of Structure III are used in the compositions of the present invention at a concentration less than about 8.0 by weight (wt %), preferably less than about 5.0 wt %.

The active ingredient or ingredients which can be included in the compositions of the present invention include all ophthalmic agents which can be topically applied. Such ophthalmic agents include (but are not limited to): glaucoma agents, such as beta-blockers (e.g., betaxolol and timolol), muscarinics (e.g., pilocarpine) and carbonic anhydrase inhibitors (e.g., acetazolamide, methazolamide and ethoxzolamide); dopaminergic agonists and antagonists; post-surgical ∝-2 agonists, such as para-amino clonidine (also known as apraclonidine); anti-infectives, such as ciprofloxacin; non-steroidal and steroidal anti-inflammatories, such as suprofen, ketorolac and tetrahydrocortisol; prostaglandins; proteins; growth factors, such as EGF; and anti-allergics. Compositions of the present invention may also include combinations of ophthalmic agents.

The compositions of the present invention can also include other components, for example, ophthalmically acceptable buffers, preservatives, and tonicity agents. As will be appreciated by those skilled in the art, the compositions may be formulated in various dosage forms suitable for topical ophthalmic delivery, including solutions, suspensions, emulsions, gels and erodible solid ocular inserts.

The following examples are presented to illustrate further various aspects of the present invention, but are not intended to limit the scope of the invention in any respect.

EXAMPLE 1

| Ingredient | Percent (w/w) |
| --- | --- |
| Betaxolol HCl | 0.28 + 5% xs |
| Amberlite ® IRP-69 | 0.25 |
| Carbopol ® 934P | 0.2 |
| Hamposyl ® L | 0.03 |
| Boric Acid | 0.6 |
| Mannitol | 4.5 |
| EDTA | 0.01 |
| BAC | 0.01 + 10% xs |
| NaOH and/or HCl | q.s. to pH 6.6 |
| Purified Water | q.s. to 100 |

Preparation:

To a solution of 0.29 grams ("g") of betaxolol HCl in 50 milliliters ("ml") of purified water was added 0.250 g of Amberlite® IRP-69. The suspension was stirred for 12 hrs, at which time 10 ml of 2% Carbopol® 934P slurry, 4.5 g of mannitol, 0.6 g of boric acid, 0.01 g of EDTA and 1.1 ml of 1% BAC solution were added with continuous stirring. Batch weight was brought to 70 g with purified water and pH was adjusted to 7.6±0.2 with sodium hydroxide.

The suspension was autoclaved for 30 minutes, and then 3 ml of 1% sterile filtered Hamposyl® L solution was added aseptically. Formulation batch weight was then brought to 100 g with sterile purified water and final pH was adjusted to 7.6, as necessary.

EXAMPLE 2

| Ingredient | Percent (w/w) |
| --- | --- |
| Timolol Maleate | 0.34 |
| Amberlite ® IRP-69 | 0.25 |
| Carbopol ® 934P | 0.2 |
| Mannitol | 4.5 |
| Hamposyl ® L | 0.09 |
| EDTA | 0.01 |
| BAC | 0.01 + 10% xs |
| NaOH and/or HCl | q.s. to pH 7.0 |
| Purified Water | q.s. to 100 |

Preparation:

To a solution of 0.34 g of timolol maleate in 50 g of purified water was added 0.25 g of Amberlite® IRP-69. The suspension was stirred for 12 hrs, at which time 10 ml of 2% Carbopol® 934P slurry, 4.5 g of mannitol, 1.0 ml of 1% EDTA solution and 1.1 ml of 1% BAC solution were added with continuous stirring. Batch weight was brought to 80 g with purified water and pH was adjusted to 7.0 with sodium hydroxide and the suspension was autoclaved for 30 minutes. At that time, 9 ml of 1% sterile filtered Hamposyl® L solution was added aseptically. Formulation batch weight was then brought to 100 g with sterile purified water and pH was adjusted, if needed, to 7.0.

EXAMPLE 3

| Ingredient | Percent (w/w) |
| --- | --- |
| Betaxolol HCl | 0.28 + 5% xs |
| Pilocarpine HCl | 1.75 + 5% xs |
| Amberlite ® IRP-69 | 0.25 |
| Carbopol ® 934 P | 0.4 |
| Boric Acid | 0.08 |
| Mannitol | 1.76 |
| Hamposyl ® L | 0.03 |
| EDTA | 0.01 |
| BAC | 0.01 + 10% xs |
| NaOH and/or HCl | q.s. to pH |
| Purified Water | q.s.to 100 |

Preparation:

A) Betaxolol Suspension: To a solution of 0.294 g of betaxolol HCl in 20 ml of purified water was added 0.250 g of Amberlite® IRP-69. The suspension was stirred for a minimum of 12 hrs, at which time 20.0 g of Carbopol® 934P slurry, 1.76 g of mannitol, 0.08 g of boric acid, 0.01 g of EDTA, and 1.1 g of 1% BAC solution were added with continuous stirring. Batch weight was adjusted to 65 g with purified water and pH was adjusted to 8.0±0.2 with sodium hydroxide. The formulation was autoclaved for 30 minutes, and the suspension was allowed to cool to room temperature under stirring. Final batch weight was brought to 80 g with purified water under aseptic conditions and pH was adjusted to 8.0, as necessary.

B) Pilocarpine Solution: In another container, 1.838 g of pilocarpine HCl was dissolved in 10 ml of purified water and pH of the solution was adjusted to 5.0 ±0.2 with sodium hydroxide. This solution was sterile filtered through a 0.2 μ filter and 3 ml of 1% sterile filtered Hamposyl® L solution was added aseptically to the pilocarpine solution. Batch weight of the final formulation was brought to 20 g and pH was adjusted to 5.0, as necessary.

When reconstituted together, Parts A and B provide the composition of Example 3.

EXAMPLE 4

| Ingredient | Percent (w/w) |
| --- | --- |
| Betaxolol HCl | 0.28 |
| Dipivefrin HCl | 0.1 |
| Amberlite ® IRP-69 | 0.25 |
| Carbopol ® 934P | 0.35 |
| Boric Acid | 1.25 |
| Mannitol | 0.5 |
| Hamposyl ® L | 0.06 |
| EDTA | 0.01 |
| Sodium Metabisulfite | 0.04 |
| BAC | 0.01 + 5% xs |
| NaOH and/or HCl | q.s. to pH 7.0 |
| Purified Water | q.s. to 100 |

Preparation:

A) Betaxolol Suspension: To a solution of 0.28 g of betaxolol HCl in 20 ml of purified water was added 0.250 g of Amberlite® IRP-69 under continuous stirring for a minimum of 12 hours. Carbopol® 934P slurry (0.35 g) was added and stirred well, then 0.5 g of mannitol, 0.01 g of EDTA and 1.1 g of 1% BAC solution were added with continuous stirring. Boric acid (1.25 g) was then added with stirring until dissolved. Batch weight was brought to 40 g with purified water and pH was adjusted to 7.0 with sodium hydroxide, and the formulation was autoclaved for 30 minutes. The Hamposyl® L (5% sterile solution) was then added to the solution with continuous stirring. Batch weight was brought to 50 g with purified water and pH was adjusted, if needed, to 7.0.

B) Dipivefrin Solution: To a solution of 0.11 g of dipivefrin HCl in 30 ml of purified water was added 0.04 g of sodium metabisulfite with continuous stirring. The formulation pH was adjusted to 3.2±0.2 with sodium hydroxide, the batch weight was brought to 50 g with sterile purified water, and the formulation sterile filtered.

When reconstituted together, Parts A and B provide the composition of Example 4.

EXAMPLE 5

| Ingredient | Percent (w/w) |
| --- | --- |
| Pilocarpine HCl | 4.0 + 10% xs |
| Carbopol ® 940P | 3.5 |
| EDTA | 0.01 |
| Hamposyl ® L | 0.12 |
| BAC | 0.008 + 10% xs |
| NaOH and/or HCl | q.s. to pH 4.8 |
| Purified Water | q.s. to 100 |

Preparation:

To a solution of 4.4 g of pilocarpine HCl in 15 ml of purified water were added 0.01 g of EDTA and 0.88 g of 1% BAC solution with continuous stirring. The solution was then sterile filtered, 17.5 g of 2% Carbopol® 940P slurry added and the pH adjusted to 4.8 with sterile sodium hydroxide. At that time, 4 g of 3% sterile Hamposyl® L solution was added with continuous stirring. Batch weight was then brought to 100 g with sterile purified water and pH was adjusted to 4.8, as necessary.

EXAMPLE 6

| Ingredient | Percent (w/w) |
| --- | --- |
| Ciprofloxacin HCl | 0.35 |
| Polystyrene Sulfonic Acid | 2.0 |
| Hamposyl ® L | 0.03 |
| Mannitol | 3.9 |
| BAC | 0.01 |
| NaOH and/or HCl | q.s. to pH 6.0 |
| Purified Water | q.s. to 100 |

Preparation:

To a solution of 0.35 g of ciprofloxacin HCl in 25 ml of purified water was added 40 ml of 5% PSSA (Mw=500,000) solution with stirring. At that time, 3.9 g of mannitol, and 1 ml of 1% BAC solution were added and the pH adjusted to 6.0 with sodium hydroxide. The solution was then autoclaved for 30 minutes. After autoclaving, 3 ml of 1% sterile filtered Hamposyl® L solution was added, the batch weight brought to 100 g with sterile filtered water, and the final pH was adjusted to 6.0, as necessary.

EXAMPLE 7

| Ingredient | Percent (w/w) |
| --- | --- |
| Apraclonidine HCl | 0.293 |
| Amberlite ® IRP-69 | 0.25 |
| Carbopol ® 934P | 0.2 |
| Mannitol | 4.0 |
| Hamposyl ® L | 0.18 |
| EDTA | 0.01 |
| BAC | 0.01 + 10% xs |
| NAOH and/or HCl | q.s. to pH 7.4 |
| Purified Water | q.s. to 100 |

Preparation:

To a solution of 0.293 g of apraclonidine in 30 ml of purified water was added 0.25 g of Amberlite® IRP-69. The suspension was stirred for a minimum of 12 hrs, then 10 g of 2% Carbopol® 934P slurry, 4.0 g of mannitol, 0.01 g of EDTA and 1.1 ml of 1% BAC solution were added to the suspension with continuous stirring. Batch weight was brought to 65 g with purified water, and the pH adjusted to 7.4±0.2 with sodium hydroxide. The suspension was autoclaved for 30 minutes, and then allowed to cool to room temperature with stirring. Upon cooling, 6 ml of 3% sterile filtered Hamposyl® L solution was added to the suspension, the final weight brought to 100 g with sterile filtered purified water, and the final pH adjusted to 7.4±0.2, as necessary.

EXAMPLE 8

| Ingredient | Percent (w/w) % |
| --- | --- |
| Betaxolol HCl | 0.28 + 5% xs |
| Amberlite ® IRP-69 | 0.25 |
| Carbopol ® 974P | 0.2 |
| Hamposyl ® O | 0.03 |
| Mannitol | 4.0 |
| Boric Acid | 0.6 |
| Edetate Disodium | 0.01 |
| Benzalkonium Chloride | 0.01 + 10% xs |
| NaOH and/or HCl | q.s. to pH 6.6 |
| Purified Water | q.s. to 100% |

Preparation:

The equivalent of 1.250 g of Amberlite® was weighed into a suitable 500 ml container, about 100 ml of purified water was added and the mixture stirred. Betaxolol HCl (1.47 g) was added to the Amberlite® suspension, and the mixture stirred for 12 hours. A 2% Carbopol® 974P slurry (50 ml) and 20 g of mannitol were dissolved in about 150 ml of purified water, and the mixture filtered through a 0.2 micron filter. Then 3.0 g of boric acid and 0.05 g of EDTA were added under constant stirring. The batch weight was brought to about 400 g with purified water and the pH was adjusted to 6.6 with sodium hydroxide.

The suspension formulation was autoclaved for 45 minutes, then 5 g of a sterile filtered 3% Hamposyl® O solution was aseptically added to the suspension. After stirring the suspension for 3 hours, 5.5 g of a sterile filtered 1% benzalkonium chloride solution were added, the batch was brought to 500 g with purified water and the final pH was adjusted to 6.6.

The invention in its broader aspects is not limited to the specific details shown and described above. Departures may be made from such details within the scope of the accompanying claims without departing from the principles of the invention and without sacrificing its advantages.

What is claimed is:

1. A method of improving or enhancing the antimicrobial efficacy of an ophthalmic composition comprising a cationic antimicrobial, an anionic polyelectrolyte and an active ingredient, said method comprising adding to said composition an antimicrobial-enhancing amount of an anionic surfactant selected from the group consisting of:

a) a compound of formula:

$$\left[ R^1-\underset{\underset{O}{\|}}{C}-\underset{\underset{}{|}}{\underset{CH_3}{N}}-CH_2-C\underset{\diagdown O}{\overset{\diagup O^-}{\phantom{C}}} \right]_n M^+ \qquad I$$

wherein: $R^1 = C_4-C_{27}$ saturated or unsaturated hydrocarbon;

M=H or a pharmaceutically acceptable salt; and n=1, 2 or 3; and b) a compound of formula:

$$\left[ R^2-\underset{\underset{}{\|}}{\overset{O}{C}}-O-\underset{\underset{CH_3}{|}}{\overset{H}{\underset{}{C}}}-\underset{\underset{}{\|}}{\overset{O}{C}}-O-\underset{\underset{CH_3}{|}}{\overset{H}{\underset{}{C}}}-C\underset{\diagdown O}{\overset{\diagup O^-}{\phantom{C}}} \right]_n M^+ \qquad II$$

wherein: $R^2 = C_4-C_{27}$ saturated or unsaturated hydrocarbon;

M=H or a pharmaceutically acceptable salt; and n=1, 2 or 3.

2. The method of claim 1, wherein the final composition concentration of said anionic surfactant is between about 0.005 and about 5.0 wt %.

3. The method of claim 2, wherein said anionic surfactant comprises a compound of formula I.

4. The method of claim 3, wherein the final composition concentration of said anionic surfactant is between about 0.005 and about 0.5 wt %.

5. The method of claim 4, wherein the final composition concentration of said anionic surfactant is between about 0.01 and about 0.2 wt %.

6. The method of claim 5, wherein the final composition concentration of said anionic surfactant is between about 0.03 and about 0.12 wt %.

7. The method of claim 2, wherein said anionic surfactant comprises a compound of formula II.

8. The method of claim 7, wherein the final composition concentration of said anionic surfactant is between about 0.1 and about 5.0 wt %.

9. The method of claim 8, wherein the final composition concentration of said surfactant is between about 0.1 and about 2.0 wt %.

10. The method of claim 9, wherein the final composition concentration of said surfactant is about 0.5 wt %.

11. The method of claim I wherein said surfactant is selected from the group consisting of lauroyl sarcosine, oleoyl sarcosine, myrstoyl sarcosine, cocoyl sarcosine, stearoyl sarcosine, pelargodoyl sarcosine and sodium capryl lactylate.

12. The method of claim 1, wherein said cationic antimicrobial comprises benzalkonium chloride.

13. The method of claim 1, wherein said anionic polyelectrolyte is selected from the group consisting of: carboxyvinyl polymers, polystyrene sulfonic acid polymers and finely divided cationic exchange resins.

14. The method of claim 13, wherein said anionic polyelectrolyte comprises a carboxyvinyl polymer.

15. The method of claim 13, wherein said anionic polyelectrolyte comprises a polystyrene sulfonic acid polymer of formula:

III
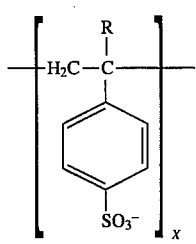
wherein: R=H or CH$_3$; and
X=an integer such that the molecular weight of the polystyrene sulfonic acid polymer may vary from about 10,000 to 1.6 million.
16. The method of claim 13, wherein said anionic polyelectrolyte comprises a finely divided cationic exchange resin.
* * * * *